United States Patent
Shimizu et al.

(10) Patent No.: US 8,266,129 B2
(45) Date of Patent: Sep. 11, 2012

(54) SYSTEM FOR ENDOSCOPE DATA MANAGEMENT, AND SYSTEM AND DATA MANAGER FOR WASHING DATA MANAGEMENT

(75) Inventors: Kunimasa Shimizu, Tokyo (JP); Takayuki Goto, Tokyo (JP); Goro Miura, Tokyo (JP); Takayoshi Kiuchi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 943 days.

(21) Appl. No.: 12/252,840

(22) Filed: Oct. 16, 2008

(65) Prior Publication Data
US 2009/0103836 A1    Apr. 23, 2009

(30) Foreign Application Priority Data
Oct. 17, 2007 (JP) ................................. 2007-270722

(51) Int. Cl.
*G06F 7/00* (2006.01)
*G06F 17/30* (2006.01)

(52) U.S. Cl. ........ 707/705; 382/305; 600/117; 600/118; 600/101; 705/2; 705/3; 134/58 R; 134/3; 702/1; 702/33; 702/34; 702/35; 702/127; 702/182; 702/187; 73/865.8; 340/500; 340/540; 340/679; 340/870.01; 340/870.07; 340/870.16; 377/1; 377/15; 377/16

(58) Field of Classification Search ................. 382/305; 600/117, 118, 101; 705/2, 3; 134/58 R; 707/705; 702/1, 33, 34, 35, 127, 182, 187; 73/865.8; 340/500, 540, 679, 870.01, 870.07, 340/870.16; 377/1, 15, 16
See application file for complete search history.

(56) References Cited

U.S. PATENT DOCUMENTS

| 4,667,229 A | * | 5/1987 | Cooper et al. ................. 348/71 |
| 4,862,872 A | | 9/1989 | Yabe et al. |
| 5,209,220 A | * | 5/1993 | Hiyama et al. ................ 600/109 |
| 6,424,996 B1 | * | 7/2002 | Killcommons et al. ...... 709/206 |

(Continued)

FOREIGN PATENT DOCUMENTS
EP    1 155 654 A1    11/2001

(Continued)

OTHER PUBLICATIONS

EP Communication, dated Mar. 5, 2009, issued in corresponding EP Application No. 08018161.3, 7 pages.

(Continued)

*Primary Examiner* — Michael Kornakov
*Assistant Examiner* — Katelyn Whatley
(74) *Attorney, Agent, or Firm* — Sughrue Mion, PLLC

(57) ABSTRACT

A system for endoscope data management of an endoscopic image of a body acquired by an endoscope is provided. An image filing apparatus retrieves the image from the endoscope, and records data of the image and scope ID assigned to the endoscope in association with one another. A washer washes the endoscope. A memory is incorporated in the washer, for storing log information of washing of the endoscope. A data manager retrieves the log information on line with the washer, to record the scope ID and the log information in association with one another. A server device records the data of the image, the scope ID and the log information on line with the image filing apparatus and the data manager. Furthermore, the data manager includes an editor for editing the log information of the washer.

5 Claims, 11 Drawing Sheets

U.S. PATENT DOCUMENTS

| | | | |
|---|---|---|---|
| 6,436,032 B1* | 8/2002 | Eto et al. | 600/117 |
| 6,447,446 B1* | 9/2002 | Smith et al. | 600/157 |
| 6,581,117 B1* | 6/2003 | Klein et al. | 710/110 |
| 6,638,212 B1* | 10/2003 | Oshima | 600/109 |
| 6,726,620 B2* | 4/2004 | Shibata et al. | 600/118 |
| 7,193,519 B2* | 3/2007 | Root et al. | 340/573.1 |
| 7,255,676 B2* | 8/2007 | Higuchi et al. | 600/118 |
| 7,366,992 B2* | 4/2008 | Thomas, III | 715/764 |
| 7,547,277 B2* | 6/2009 | Wiklof et al. | 600/117 |
| 7,606,861 B2* | 10/2009 | Killcommons et al. | 709/206 |
| 7,660,420 B1* | 2/2010 | Narayan et al. | 380/274 |
| 7,670,283 B2* | 3/2010 | Araki | 600/117 |
| 7,844,657 B2* | 11/2010 | Novak | 709/200 |
| 7,957,982 B2* | 6/2011 | Omoto et al. | 705/2 |
| 8,125,515 B2* | 2/2012 | Hibi | 348/65 |
| 2001/0041825 A1* | 11/2001 | Shibata et al. | 600/118 |
| 2002/0161460 A1* | 10/2002 | Noguchi | 700/90 |
| 2002/0184325 A1* | 12/2002 | Killcommons et al. | 709/206 |
| 2004/0041031 A1* | 3/2004 | Root et al. | 235/487 |
| 2004/0107113 A1* | 6/2004 | Araki | 705/1 |
| 2005/0065400 A1* | 3/2005 | Banik et al. | 600/109 |
| 2005/0070761 A1* | 3/2005 | Higuchi | 600/109 |
| 2006/0293563 A1* | 12/2006 | Banik et al. | 600/117 |
| 2007/0061393 A1* | 3/2007 | Moore | 709/201 |
| 2007/0185385 A1* | 8/2007 | Noguchi et al. | 600/132 |
| 2007/0219413 A1* | 9/2007 | Lin | 600/160 |
| 2007/0286764 A1* | 12/2007 | Noguchi et al. | 422/3 |
| 2008/0120372 A1* | 5/2008 | Kariathungal et al. | 709/204 |
| 2008/0162184 A1* | 7/2008 | Matsubara et al. | 705/2 |
| 2009/0103836 A1* | 4/2009 | Shimizu et al. | 382/305 |
| 2009/0125337 A1* | 5/2009 | Abri | 705/3 |
| 2009/0192354 A1* | 7/2009 | Hasegawa | 600/118 |
| 2009/0307328 A1* | 12/2009 | Nuttall et al. | 709/212 |
| 2010/0083303 A1* | 4/2010 | Redei et al. | 725/32 |
| 2010/0094101 A1* | 4/2010 | Koike et al. | 600/300 |

FOREIGN PATENT DOCUMENTS

| | | |
|---|---|---|
| JP | 2006-051073 A | 2/2006 |
| JP | 3791894 B2 | 6/2006 |
| JP | 2007-202604 A | 8/2007 |

OTHER PUBLICATIONS

Notification of Reasons for Refusal, dated Apr. 25, 2012, issued in corresponding JP Application No. 2007-270722, 4 pages in English and Japanese.

\* cited by examiner

FIG. 3

| WASHING SER NO | CATEGORY | DATE | WASHING SEQUENCE (PG_NO) | START TIME | END TIME | USE OF DISINFECTANT | USE OF FILTER |
|---|---|---|---|---|---|---|---|
| 1 | WASH/ DISINFECT | 8/23 | 1 | 13:20 | 17:30 | 1 TIME | 1 DAY |

41a

| PATIENT ID | PATIENT'S NAME | SCOPE ID (SCP_ID) | WASHING OPERATOR | OPERATION MODE |
|---|---|---|---|---|
| A0102 | EMILY YAMADA | E012 | JOHN FUJI | BIOPSY |

41b

41

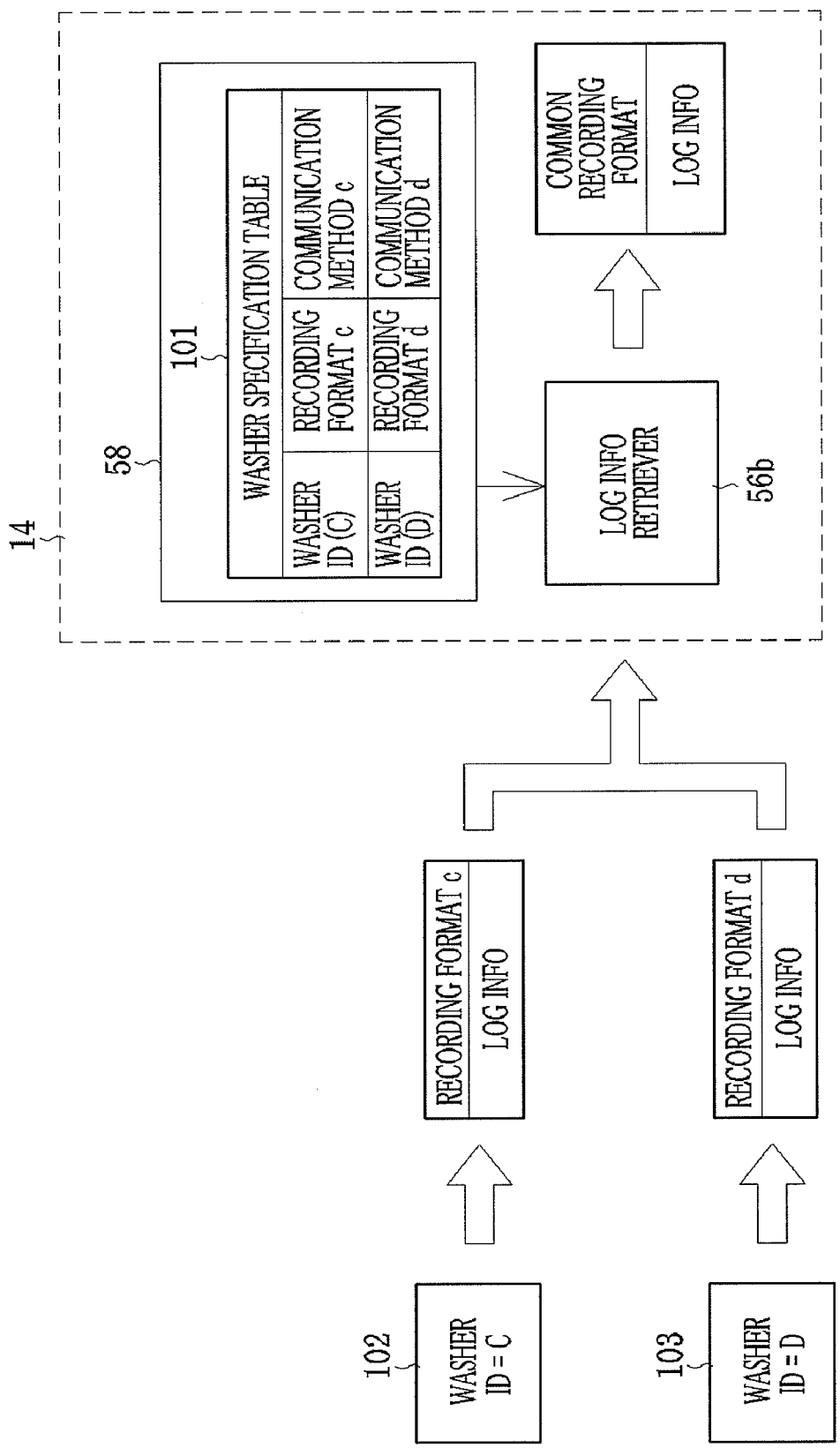

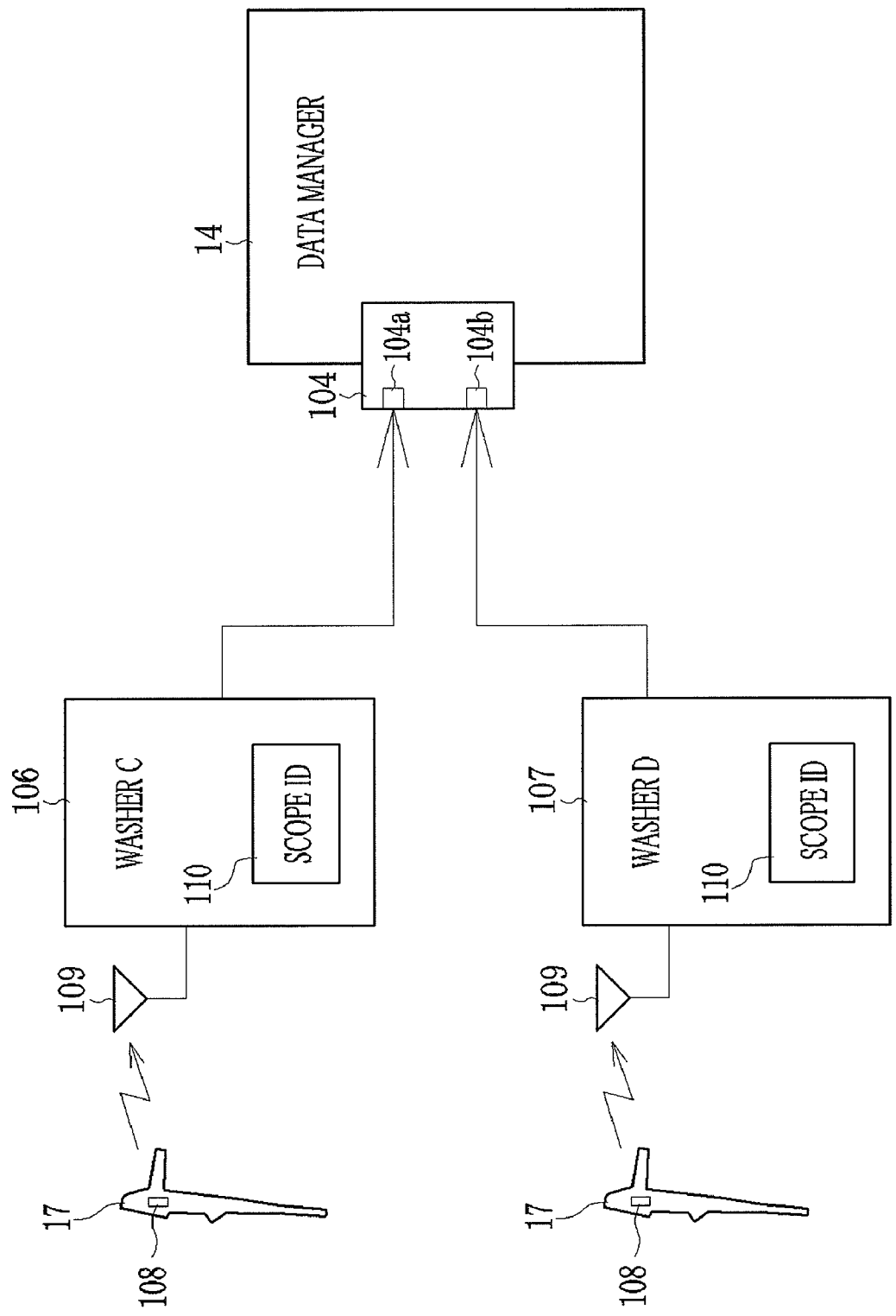

SYSTEM FOR ENDOSCOPE DATA MANAGEMENT, AND SYSTEM AND DATA MANAGER FOR WASHING DATA MANAGEMENT

BACKGROUND OF THE INVENTION

1. Field of the Invention

The present invention relates to a system for endoscope data management, and a system and data manager for washing data management. More particularly, the present invention relates to a system for endoscope data management, and a system and data manager for washing data management in which washing information associated with an endoscope can be managed with high efficiency and reliability without lowering the system availability.

2. Description Related to the Prior Art

A system for endoscope data management is disclosed in U.S. Pat. No. 6,726,620 (corresponding to JP-B 3791894). In image filing, the system for endoscope data management manages an endoscopic image acquired by an endoscope in an endoscope apparatus examining a patient's gastrointestinal tract. Also, in washing data management, washing information of the endoscope is managed. The system for endoscope data management includes the endoscope apparatus, a washer, and an image filing apparatus. The endoscope apparatus includes the endoscope and a processor. The washer washes the endoscope.

The washer operates for recording and outputting data. In the recording, washing log information is recorded, including information of a start time and end time of washing of the endoscope, method of washing and the like. In the outputting, the washer sends the log information to the image filing apparatus. The image filing apparatus is on line with each of the endoscope and the washer, and receives data of the endoscopic image and the washing information from those, and writes the data to storage which is connected locally with the image filing apparatus. The endoscopic image and the washing information are stored in associated with the scope ID. Thus, it is possible to manage all the information including data of the endoscopic image and the washing information relation to the endoscope.

However, the image filing apparatus in the system for endoscope data management operates not only for filing image data output by the endoscope but for storing the washing information output by the washer. Load applied to the image filing apparatus is excessively high specifically when washing is carried out at the same time as examination. This will lower the processing speed of the image filing apparatus. Furthermore, failure occurring in the communication between the image filing apparatus and the washer will be an obstacle to both of the examination and washing. The excessive load to the image filing apparatus will lower the availability of the entirety of the system for endoscope data management.

It is also likely that there are difference between the recording format of the washing information, communication method and other specifications between a plurality of the washers or between their manufacturers. This is a problem in the concentrated management of the washing information output by the washers. In the system for endoscope data management of the known technique, the image filing apparatus directly receives the washing information from the washers. Additional tasks must be performed by the image filing apparatus in compliance with the specifications of the washers for the purpose of communication. Load to the image filing apparatus may be still higher due to the data management of the washing information.

SUMMARY OF THE INVENTION

In view of the foregoing problems, an object of the present invention is to provide a system for endoscope data management, and a system and data manager for washing data management in which washing information associated with an endoscope can be managed with high efficiency and reliability without lowering the system availability.

In order to achieve the above and other objects and advantages of this invention, a system for endoscope data management of an endoscopic image of a body acquired by an endoscope is provided. An image filing apparatus retrieves the image from the endoscope, and records data of the image and endoscope identification information assigned to the endoscope in association with one another. A washer washes the endoscope. A memory is incorporated in the washer, for storing log information of washing of the endoscope. A data manager retrieves the log information by communication with the washer, to record the endoscope identification information and the log information in association with one another. A server device records the data of the image, the endoscope identification information and the log information by communication with the image filing apparatus and the data manager according to a control signal thereof.

The data manager includes an editor for editing the log information of the washer.

The washer is constituted by plural washers. The data manager further includes a designator for designating one of the washers associated with the log information being retrieved.

The data manager includes a washer specification table memory for storing specification information in association with the washers, the specification information being related to at least one of a recording format of recording the log information in the washers and information of a communication method of the washers. A data retriever refers to the specification information in the washer specification table memory, to retrieve the log information from the washer designated by the designator.

If a first recording format of recording of the log information in the designated washer is different from a predetermined recording format according to the specification information assigned to the designated washer, the data retriever converts the log information into the predetermined recording format.

In one preferred embodiment, if a first communication method in the designated washer for transmitting the log information is different from a predetermined communication method according to the specification information assigned to the designated washer, the data retriever changes over control to the first communication method to retrieve the log information.

The data manager includes a storage changer for operating upon occurrence of failure in writing of the log information to the server device, and for changeover to an auxiliary storage medium to write the log information thereto.

The auxiliary storage medium is locally connected with the data manager.

The data manager includes a reader for reading the endoscope identification information from the endoscope.

In one preferred embodiment, the washer includes a reader for reading the endoscope identification information from the endoscope.

Also, a system for washing data management with plural washers for washing respectively an endoscope is provided. A memory is incorporated in each of the washers, for storing log information of washing of the endoscope. In the system for washing data management, a data manager retrieves endoscope identification information assigned to the endoscope and the log information by communication with respectively the washers, to record the endoscope identification information and the log information in association with one another. A designator is disposed in the data manager, for designating one of the washers associated with the log information being retrieved. A server device records the endoscope identification information and the log information by communication with the data manager according to a control signal thereof.

Furthermore, an editor edits the log information of the designated washer.

Also, a data manager for washing data management of washing of an endoscope is provided. A data retriever retrieves log information of the washing by communication with washers for washing respectively the endoscope. An assigning unit records endoscope identification information assigned to the endoscope and the log information in association with one another. A designator designates one of the washers associated with the log information being retrieved.

Furthermore, an editor edits the log information of the designated washer.

Furthermore, an access unit accesses a washer specification table memory to read specification information being related to at least one of a recording format of recording the log information in the washers and information of a communication method of the washers. The data retriever refers to the specification information in the washer specification table memory, to retrieve the log information from the washer designated by the designator.

Furthermore, a storage changer operates upon occurrence of failure in writing of the log information, for changeover to an auxiliary storage medium to write the log information thereto.

The auxiliary storage medium is locally connected, and in case of failure in normal completion of writing to a storage medium on line through a network, the storage changer changes over to the auxiliary storage medium.

Furthermore, a reader reads the endoscope identification information from the endoscope.

In a preferred embodiment, a method of washing data management with plural washers for washing respectively an endoscope is provided. A memory is incorporated in each of the washers, for storing log information of washing of the endoscope. In the method of washing data management, endoscope identification information assigned to the endoscope and the log information by communication with respectively the washers is retrieved, to record the endoscope identification information and the log information in association with one another. One of the washers associated with the log information being retrieved is designated.

Furthermore, there is a step of editing the log information of the designated washer.

Also, a computer-executable program for washing data management with plural washers for washing respectively an endoscope is provided. A memory is incorporated in each of the washers, for storing log information of washing of the endoscope. The computer-executable program for washing data management includes a retrieving program code for retrieving endoscope identification information assigned to the endoscope and the log information by communication with respectively the washers, to record the endoscope identification information and the log information in association with one another. A designating program code is for designating one of the washers associated with the log information being retrieved.

Furthermore, there is an editing program code for editing the log information of the designated washer.

Also, a user interface for washing data management with plural washers for washing respectively an endoscope is provided. A memory is incorporated in each of the washers, for storing log information of washing of the endoscope. The user interface for washing data management includes a washer area for displaying information of the plural washers. A log information area displays the log information retrieved by communication with respectively the washers in relation to washing of the washers. A washer selection region designates one of the washers associated with the log information being retrieved.

Furthermore, there is an editing area for editing the log information of the designated washer.

Consequently, washing information associated with an endoscope can be managed with high efficiency and reliability without lowering the system availability, because the washing information is managed in the data manager which is separate from the image filing apparatus.

BRIEF DESCRIPTION OF THE DRAWINGS

The above objects and advantages of the present invention will become more apparent from the following detailed description when read in connection with the accompanying drawings, in which:

FIG. 3 is a chart illustrating a washing information record;

FIG. 10 is a block diagram schematically illustrating one preferred embodiment in which plural washers with different specifications are connectable;

FIG. 11 is a block diagram schematically illustrating another preferred embodiment with an interface converter and an RFID reader.

DETAILED DESCRIPTION OF THE PREFERRED EMBODIMENT(S) OF THE PRESENT INVENTION

Figure 1:
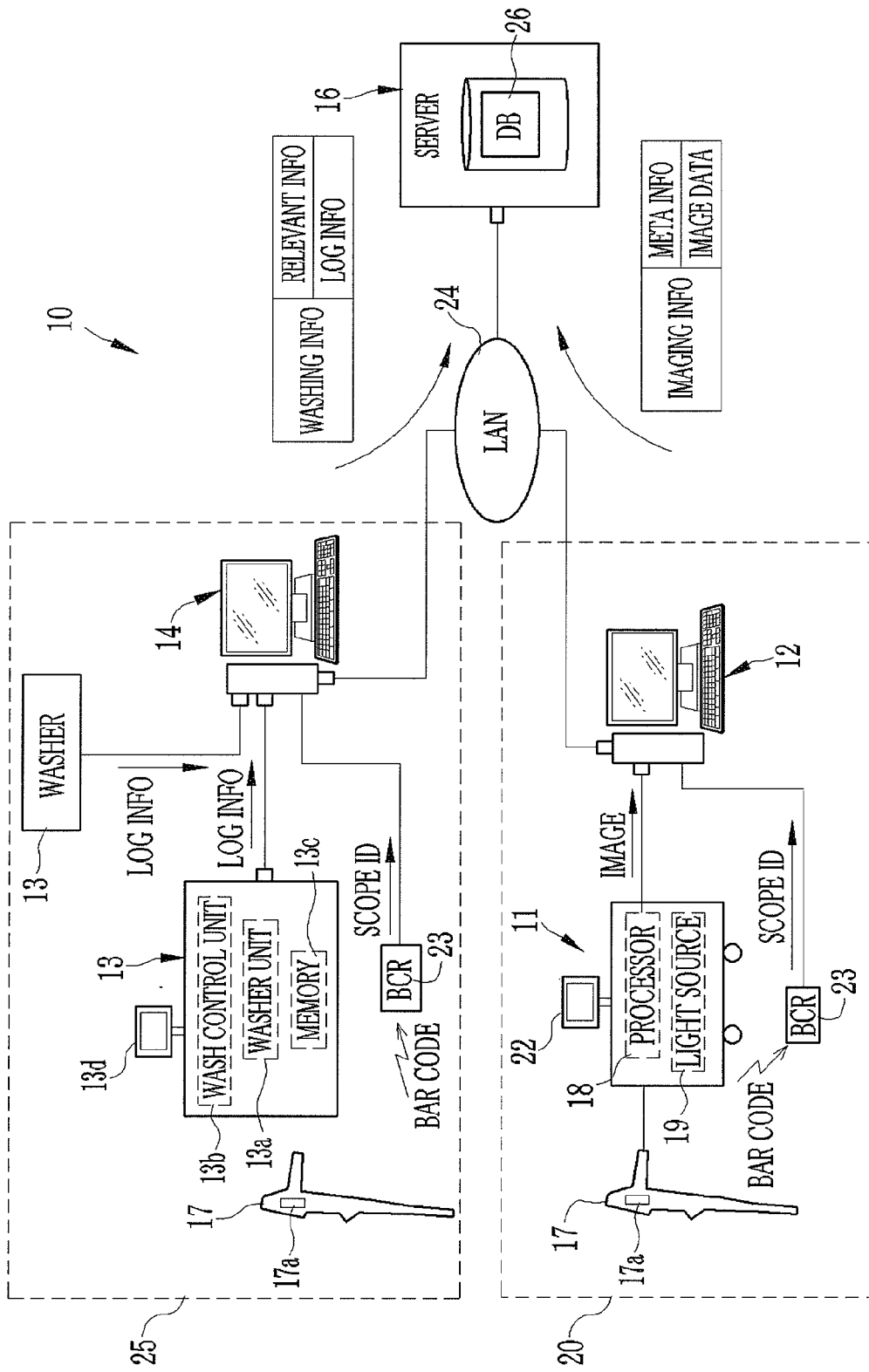
FIG. 1 is a block diagram schematically illustrating a system for endoscope data management.

In FIG. 1, a system for endoscope data management 10 is installed in a hospital as medical facilities. The system for endoscope data management 10 includes an endoscope apparatus 11, an image filing apparatus 12, a washer 13, a data manager 14 and a server device 16. The system for endoscope data management 10 manages imaging information recorded in the server device 16 by the image filing apparatus 12 and washing information recorded in the server device 16 by the data manager 14. The imaging information is constituted by image data and meta information as examination basic information. The image data is data of an endoscopic image acquired by the endoscope apparatus 11. The meta information is assigned to the endoscopic image by the image filing apparatus 12. The washing information is constituted by log information and relevant information. The log information is related to washing and recorded by the washer 13. The relevant information is assigned to the log information by the data manager 14.

The endoscope apparatus 11 includes an electronic endoscope 17, a processor 18, and a light source 19. The endoscope 17 is orally swallowed in a gastrointestinal tract, and has a head or image pickup device, such as a CCD, CMOS or the like. The processor 18 produces an endoscopic image according to an image signal output by the endoscope 17. The light source 19 generates light for lighting an object of interest as a target through the endoscope 17. There is an examination room 20 where the endoscope apparatus 11 is installed for endoscopic examination. A scope ID is assigned to the endoscope 17 as endoscope identification information. A bar code 17a is determined to express the scope ID, and printed on a sheet attached to the endoscope 17.

A cart 21 contains the processor 18 and the light source 19. A monitor display panel 22 is attached to the cart 21, and receives a signal from the processor 18 to display an endoscopic image. A doctor operates the endoscope 17 for insertion in a patient's body by observing the monitor display panel 22. The processor 18 is on line with the image filing apparatus 12, and outputs image data of a motion image or still image obtained by the examination to the image filing apparatus 12.

In the hospital is a LAN (Local Area Network) 24, through which the image filing apparatus 12 is connected to the server device 16. A bar code reader (BCR) 23 of the image filing apparatus 12 reads the bar code 17a from the endoscope 17. The image filing apparatus 12 retrieves the scope ID by use of the bar code reader 23. The image filing apparatus 12 assigns the meta information as examination basic information to image data of endoscopic images acquired by the endoscope apparatus 11, the meta information including patient information of a patient, the scope ID of the endoscope 17 used in the examination, and the like. The image filing apparatus 12 records the data in the imaging information to the server device 16 in the operation of the data recording. Also, the image filing apparatus 12 operates according to the patient information or input keywords, and searches imaging information stored in the server device 16, and also produces a medical report by utilizing the imaging information.

The washer 13 washes the endoscope 17 being used for reuse by reprocessing. A wash room 25 is separate from the examination room 20, and has the washer 13 installed therein. The washer 13 includes a washer unit 13a, a wash control unit 13b, a memory 13c and an input interface 13d. The washer unit 13a performs a task of washing. The wash control unit 13b controls the washer unit 13a. The memory 13c stores log information related to the washing. The task of washing includes washing of a narrow meaning, and at least one of disinfection and reprocessing of the endoscope 17, for example sterilization. The washer 13 records log information related to any one of those.

A washing operator operates the input interface 13d and inputs various signals, which are a request for selection of a category or a washing sequence to determine conditions of washing, and a signal of starting washing. Examples of the category include a combination of both washing and disinfection, and only disinfection. Examples of the washing sequences are a length of time taken for washing and disinfection, and the like. The wash control unit 13b controls the operation of the washer unit 13a according to the input request. The wash control unit 13b writes log information to the memory 13c for each one event of washing, the log information including the selected category and washing sequence, start time and end time of the washing, the number of times of using the disinfectant, the number of days of using a filter, and the like. The washer 13 is on line with the data manager 14, and sends the log information from the memory 13c to the data manager 14.

The data manager 14 is connected with a plurality of the washers 13, and assigns the log information retrieved from the washers 13 with relevant information including the scope ID of a scope to be washed. The data manager 14 also operates for data recording by storing washing information to the server device 16. The bar code reader 23 is also connected with the data manager 14 in a manner similar to the image filing apparatus 12, for the data manager 14 to retrieve the scope ID. The data manager 14 also is a search unit, supplied with information of an index term or key word, such as patient information, scope ID and the like, for searching washing information stored in the server device 16. This enables ordinary management of washing of the scope, and monitoring for control at the time of unwanted events, for example, for determination of source of infection and an infection route in case of hospital-acquired infection, and for prevention of spread of the infection.

The server device 16 is commonly used by the image filing apparatus 12 and the data manager 14 in connection through the LAN (local area network) in the hospital. The server device 16 receives imaging information and washing information from the image filing apparatus 12 and the data manager 14 through the LAN, and operates as a data storage server storing the information. A database (DB) 26 is configured in the server device 16 for facilitating search of the imaging information and washing information. As will be described later, the database 26 has data tables and master files. The data tables are tables of data of transaction stored after receipt from the image filing apparatus 12 and the data manager 14. The master files are files of master data as previously registered information. The server device 16 responds to requests from the image filing apparatus 12 and the data manager 14, and operates for renewing the database 26 and retrieving data from the database 26.

Figure 2:
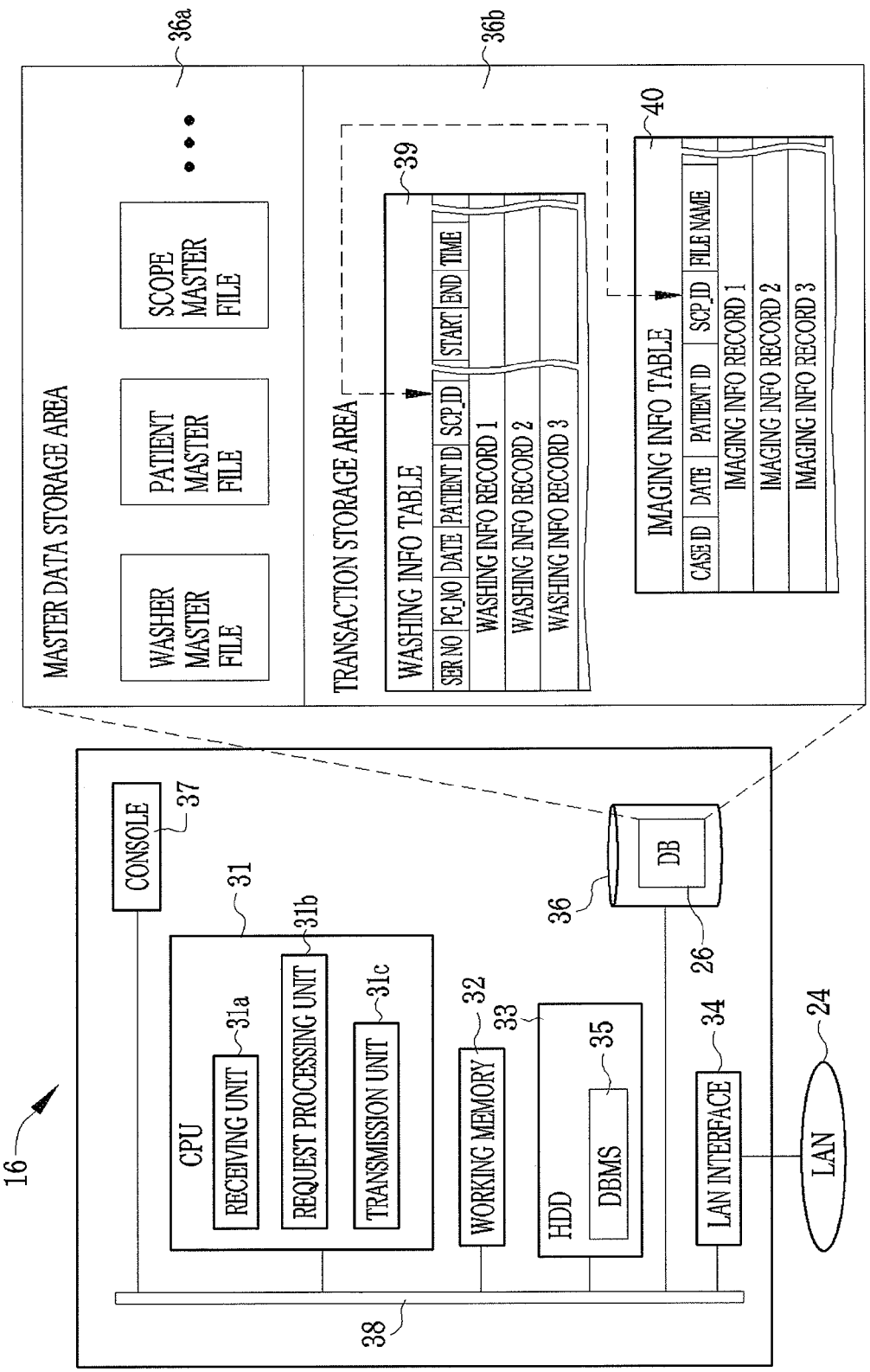
FIG. 2 is a block diagram schematically illustrating a server device.

In FIG. 2, the server device 16 is constituted by a computer and software DBMS (Database Management System). Examples of the computer are a workstation, personal computer and the like. The DBMS is installed in the computer, and manages the database. The server device 16 includes a CPU 31, a working memory 32, a HDD or hard disk drive 33, a LAN interface 34 as LAN port, a storage 36 and a console 37. The storage 36 is used to configure the database 26. There is a data bus 38 for connecting those devices. The console 37 is a user interface including a display panel and input devices such as a keyboard, mouse and the like. The console 37 is used to manage or condition the server device 16.

A DBMS 35 or database management system is installed in the hard disk drive 33. Also, an Operating System (OS) and a control program are stored in the hard disk drive 33. The CPU 31 loads the working memory 32 with the program from the hard disk drive 33, and controls various elements in the server device 16 by performing tasks according to the program. The LAN interface 34 is a network interface for communication with the LAN 24 to transmit and receive data, and is constituted by a circuit board and a connector to connect with a cable. The LAN interface 34 is according to the Ethernet (trade name) as a standardized interface in the field of LAN. The server device 16 communicates with the image filing apparatus 12 and the data manager 14 according to a communication protocol as a combination of the Ethernet (trade name) and TCP/IP (Transmission Control Protocol/Internet Protocol).

A receiving unit 31a, a request processing unit 31b and a transmission unit 31c in the CPU 31 operate by running the DBMS 35. The receiving unit 31a receives requests for a task from the image filing apparatus 12 and the data manager 14, for example, request for writing to the database 26, request for reading from the database 26, retrieval of data from the database 26 according to a designated condition. The request processing unit 31b performs a task according to the received request. The transmission unit 31c transmits a result of the task performed by the request processing unit 31b to the source of the request through the LAN interface 34.

The storage 36 includes a master data storage area 36a and a transaction storage area 36b for storing master data and data of transaction to configure the database 26. An example of the storage 36 is a disk array including a plurality of HDDs. Examples of master data include a washer master file having information of the washer ID of a plurality of the washers 13 connected with the data manager 14, a patient master file having patient information (patient ID and patient's name) of plural patients, a scope master file having information of a scope ID of a plurality of the scopes 17, and a washing operator master file having information of ID of a washing operator of the endoscope 17. Those master data are suitably renewed by use of the console 37 of the server device 16, the data manager 14 or other terminal devices. Note that the master data may be renewed not manually. For example, the patient master data may be automatically renewed by automatic retrieval of patient information from a progress note server connected with the LAN 24 or the image filing apparatus 12 through the network.

A washing information table memory 39, which stores washing information, stores data of transaction. Also, an imaging information table memory 40 which stores imaging information stores the data of the transaction. Imaging information, created at each time of examination, is stored as one imaging information record or one file. Information of the imaging information record includes meta information as examination basic information, file names of acquired images, and addresses of storage. The meta information is a data file of data such as a case ID, date of imaging, patient ID, patient's name, scope ID (SCP_ID) of the scope. The washing information table memory 39 stores washing information created at one event of washing as one washing information record or one file.

In FIG. 3, a washing information group 41 or record or data file includes log information 41a and relevant information 41b. The log information 41a is recorded by the washers 13. The relevant information 41b is constituted by the scope ID retrieved by the bar code reader 23 and information input manually with the data manager 14. The memory 13c of the washers 13 stores a washer ID, which is also read by the data manager 14 and written in an area of the washing information group 41.

Components in a data file of the log information 41a are assigned for one event of washing by the washers 13. Examples of the components in the log information 41a include a washing serial No., type of washing sequence (PG_No), date of washing, start time of washing, end time of washing, time required for washing, number of times of using disinfectant, number of days of using the filter, density of the disinfectant, and the like. The washing serial No. is identification information of the event of washing and the washing information group 41. Examples of components in a data file of the relevant information 41b are patient ID, patient's name, scope ID (SCP_ID), name of a washing operator having washed the endoscope 17, operation mode of the endoscope 17 and the like. The operation mode is relevant to the use of the endoscope 17 at the time of examination, for example, the purpose of biopsy, or the purpose of only observation without biopsy. For example, at the time of the biopsy, tissue, body liquid and the like remain stuck inside the channel of the endoscope 17 considerably in comparison with the purpose of observation. The degree of the contamination of the scope is relatively high. A level of the washing is required to be higher for the purpose of the biopsy than for the purpose of observation. The information of such examples is important for checking whether washing has been suitable in consideration of the status of the use of the scope in the monitoring for control.

The request processing unit 31b renews the database 26 by recording data transmitted from the image filing apparatus 12 or the data manager 14 in a field of a designated table. Recording of specific components in the data file makes it possible to manage the endoscope 17 in relation to identification of a patient, results of examination, identification of a washing operator, and the manner of washing. The washing information table memory 39 is constructed to refer to components in data files for common use of a query such as scope ID and the like in the imaging information table memory 40. Also, the imaging information table memory 40 is constructed to refer to components in data files for common use of a query such as scope ID and the like in the washing information table memory 39. It is thus possible in the image filing apparatus 12 to check whether the endoscope 17 has been washed or not before the examination. It is possible in the data manager 14 to read imaging information (including patient information) related to the endoscope 17 to be washed.

Note that data components and their combinations in data files of the imaging information record and washing information record according to the embodiment are only examples, and are not limited to the above-described examples. Other specific components in a data file maybe added. Also, one or more specific components in the data files may be eliminated from the above example. Although components in the data file of the washing information are caused to belong to the log information and relevant information, the belonging is not fixed but changeable. For example, the bar code reader 23 may be connected with the washers 13 to retrieve a scope ID. For this structure, the scope ID belongs to the log information.

Figure 4:
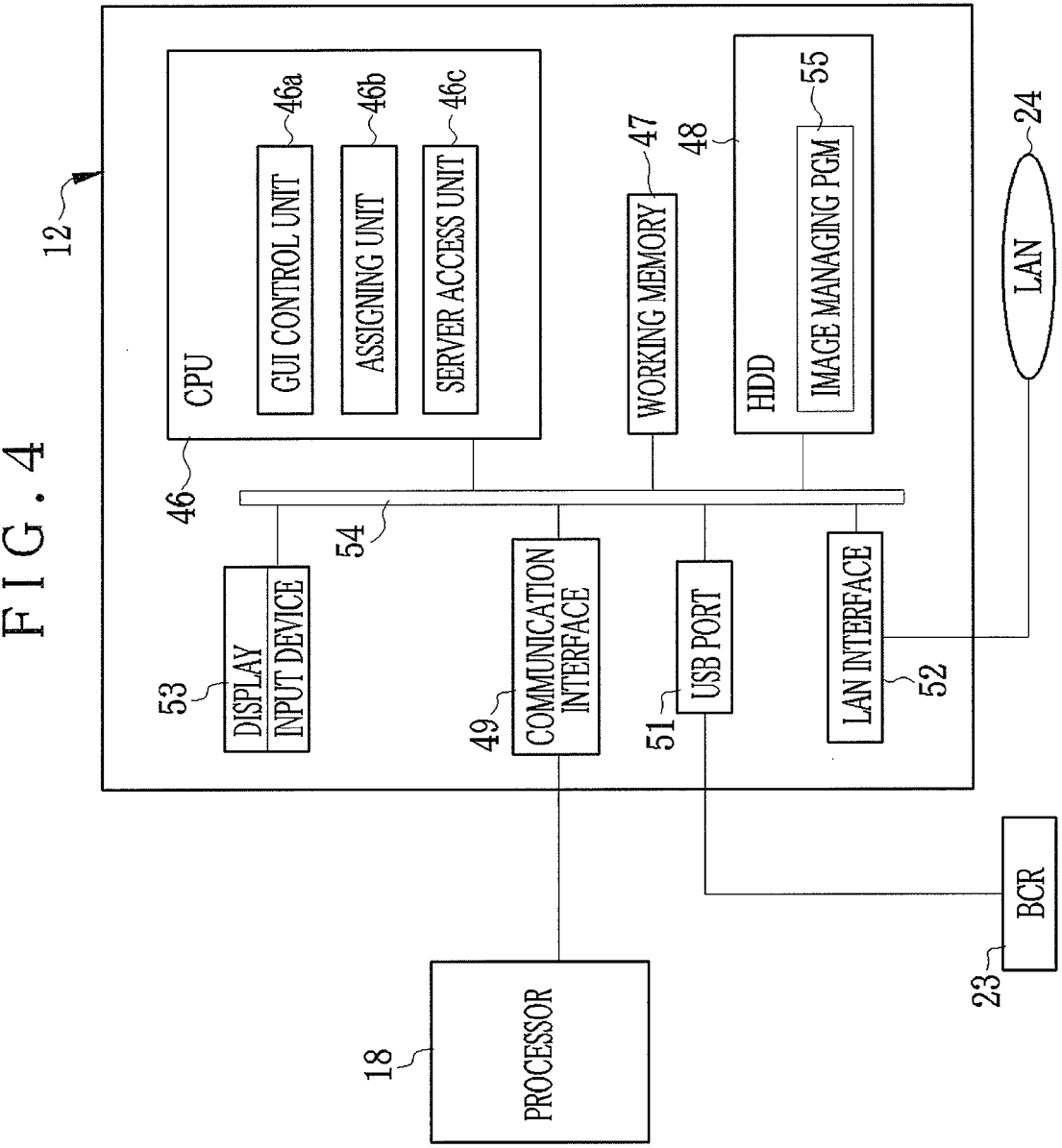
FIG. 4 is a block diagram schematically illustrating an image filing apparatus.

In FIG. 4, the image filing apparatus 12 is constituted by a workstation, personal computer or the like, and an image managing program installed therein. The image filing apparatus 12 includes a CPU 46, a working memory 47, an HDD or hard disk drive 48, a communication interface 49, a USB port 51 or Universal Serial Bus port, a LAN interface 52 as LAN port, and a console 53. A data bus 54 connects those with one another. The console 53 is a user interface including a display panel for displaying an operation window and data, and input devices such as a keyboard, mouse and the like.

An image managing program 55 is installed in the hard disk drive 48. Also, an operating system (OS) and control program are stored in the hard disk drive 48. The CPU 46 loads the working memory 47 with the program from the hard disk drive 48, and controls various elements by performing tasks according to the program. The communication interface 49 is for communication with the processor 18. An endoscopic image from the processor 18 is retrieved through the communication interface 49. The USB port 51 is for connection with the bar code reader 23. The LAN interface 52 is structurally the same as the LAN interface 34, and is a network interface for control to communicate with the LAN 24.

A GUI control unit 46a (graphical user interface control unit), an assigning unit 46b and a server access unit 46c operate in the CPU 46 when the image managing program 55 is run. The GUI control unit 46a controls the display of an operation window on the console 53, and processes a command signal input by use of the operation window. The assigning unit 46b assigns the endoscopic image with the meta information as examination basic information. The server access unit 46c outputs a request to the DBMS 35 in the server device 16 through the LAN interface 34, and receives a result of the processing of the request. The server access unit 46c outputs request of recording of imaging information to the DBMS 35, and carries out recording of imaging information including an endoscopic image. Thus, the imaging information is stored in the server device 16.

Figure 5:
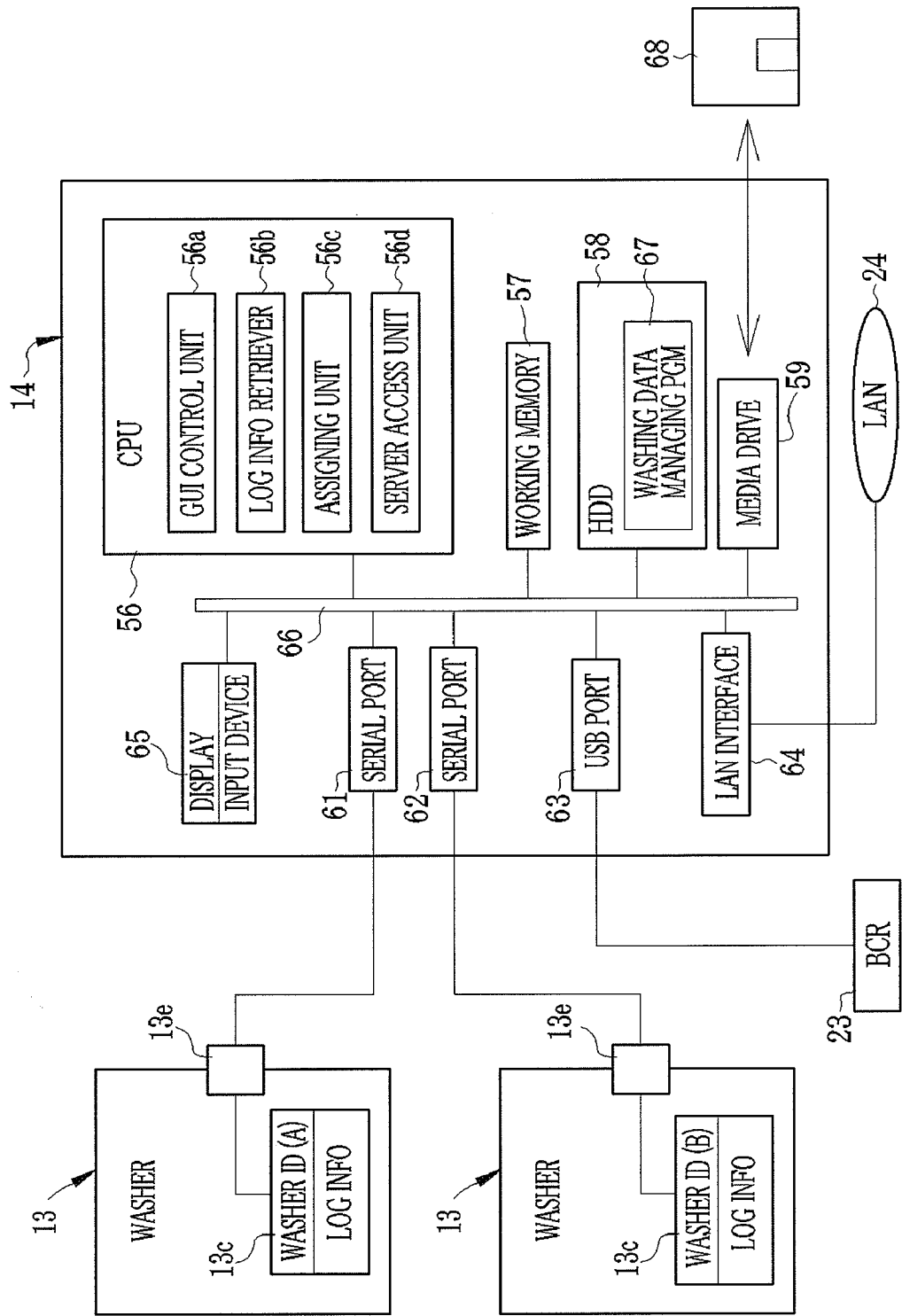
FIG. 5 is a block diagram schematically illustrating a data manager.

In FIG. 5, the data manager 14 is constituted by a computer and a washing data managing program. Examples of the computer are a workstation, personal computer and the like. The washing data managing program is installed in the computer. The data manager 14 includes CPU 56, a working memory 57, an HDD or hard disk drive 58, a media drive 59, serial ports 61 and 62, a USB port 63 or Universal Serial Bus port, a LAN interface 64 as LAN port, and a console 65. There is a data bus 66 for connecting those devices. The console 65 is a user interface including a display panel and input devices such as a keyboard, mouse and the like.

A washing data managing program 67 is installed in the hard disk drive 58. Also, an operating system (OS) and control program are stored in the hard disk drive 58. The CPU 56 loads the working memory 57 with the program from the hard disk drive 58, and controls various elements by performing tasks according to the program.

The serial ports 61 and 62 are communication interfaces to communicate with the washers 13. Log information, which is stored in the memory 13c by one of the washers 13, is retrieved by the serial port 61. The serial ports 61 and 62 are interfaces according to RS232C as standard of the serial transmission. Also, a serial port 13e is provided in each of the washers 13 and corresponds to one of the serial ports 61 and 62.

The USB port 63 is for connection with the bar code reader 23. The LAN interface 64 is structurally similar to the LAN interface 34, and constitutes a network interface for control of communication by use of the LAN 24.

A GUI control unit 56a (graphical user interface control unit), a log information retriever 56b, an assigning unit 56c and a server access unit 56d in the CPU 56 operate when the washing data managing program 67 is run. The GUI control unit 56a controls display of an operation window on the console 65, and also processes an operation signal input with the operation window. A master file stored in the server device 16 is accessed with the server access unit 56d and read by the GUI control unit 56a, and used by an operator to input information.

The log information retriever 56b carries out retrieval according to a request of the retrieval of log information. To this end, the operator operates the console 65 as designator to input a signal of the request to the CPU 56. He or she designates one of the washers 13 for the retrieval according to information previously registered in the washer master file read from the server device 16. The log information retriever 56b accesses the designated one of the washers 13 through the serial ports 61 and 62 upon receipt of the request, and retrieves log information in the memory 13c. The log information retriever 56b verifies the washer 13 as a target of the retrieval by checking the washer ID in the memory 13c with the washer ID of the washer 13 designated by the operator. Note that the washer ID of the washer 13 connected with each of the serial ports 61 and 62 may be previously stored, so that the washer 13 as a target can be designated according to the stored washer ID.

In the task of the retrieval, at first the log information retriever 56b transmits information of polling to a designated one of the washers 13, for checking existence or lack of the log information to be transmitted. The washer 13 upon receipt of the information of the polling transmits an untransmitted part of the log information to the data manager 14 from the entirety of the log information stored in the memory 13c. If all of the log information in the memory 13c remains untransmitted, then the entirety of the log information is sent to the data manager 14. If only a part of the log information remains untransmitted, then only this part is sent to the data manager 14. For an untransmitted status, a flag of remaining untransmitted is generated by the washer 13 and written to the memory 13c for management of the status.

The log information retriever 56b retrieves log information from the washers 13. Also, log information having been stored in the server device 16 after retrieval from the washer 13 is retrieved. The log information retriever 56b accesses the server device 16, and reads out washing information associated with the designated one of the washers 13 among plural sets of the washing information stored in the washing information table memory 39. Thus, all of log information on or before the request for the retrieval is retrieved in relation to the selected one of the washers 13. The entirety of the log information includes that stored in the memory 13c of the washer 13 and that stored in the server device 16. A washing data managing window 71 of FIG. 6 displays the log information, which will be described later.

The assigning unit 56c assigns the relevant information to the log information. The server access unit 56d causes the LAN interface 64 to output a request to the DBMS 35 in the server device 16, and receives a result of the task. The server access unit 56d outputs a request of storing washing information to the DBMS 35, for example designation of a table or field, and performs a task of recording the washing information after the assignment. Thus, the washing information is stored in the server device 16.

A removable auxiliary storage medium 68, such as CD, DVD and the like, is accessed by the media drive 59, which reads and/or writes data with the removable auxiliary storage medium 68. The removable auxiliary storage medium 68 is used typically in case of failure in completion of writing of data to the server device 16. Breakage is likely to occur in the LAN 24, the server device 16 or the like to cause failure in completion of writing data of the server access unit 56d to the server device 16. Then the CPU 56 as a storage changer changes over the writing from the server device 16 to the removable auxiliary storage medium 68 to back up the data.

The CPU 56 detects occurrence of errors in the LAN 24 or the server device 16 according to detection of establishment of a data link between the LAN interface 64 and the LAN 24, or according to monitor packet of the network determined by the TCP/IP, or according to response of the server device 16 for a request issued on the application level. Thus, availability of the system can be kept high by maintaining auxiliary storage of data.

Note that storage may be a medium other than the removable auxiliary storage medium 68, for example storage locally connected with the hard disk drive 58 at the data manager 14, or storage which is other than the server device 16 and on line through the LAN 24 specifically in case the LAN 24 normally operates but the server device 16 is down.

Figure 6:
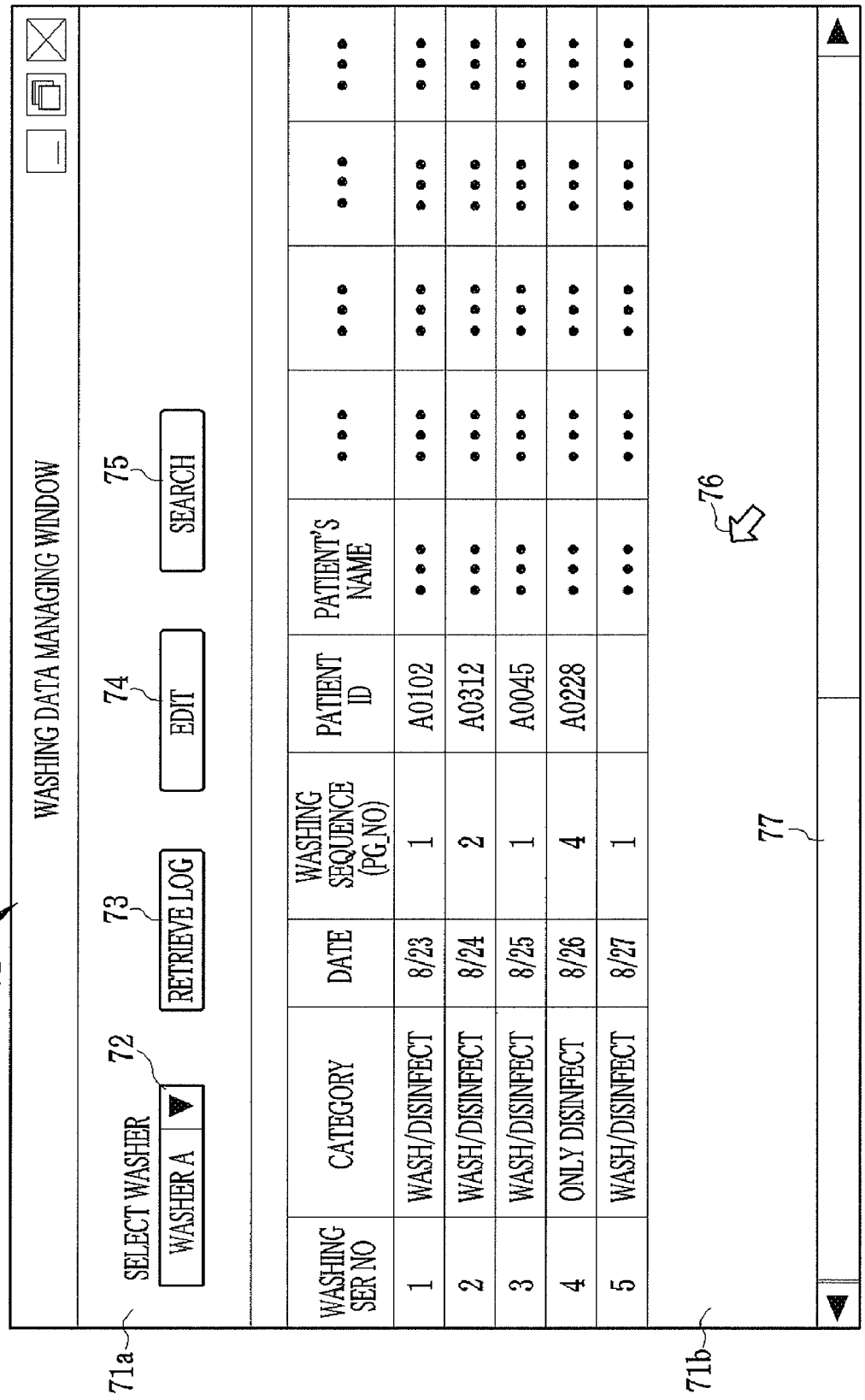
FIG. 6 is a plan illustrating an example of a washing data managing window.

In FIG. 6, the washing data managing window 71 includes an input area 71a and a log information area 71b. The log information area 71b displays washing information. The input area 71a has a washer selection region 72, a log retrieving button 73, an edit button 74 or relevant information input button, and a search button 75. The washer selection region 72 is used to designate the washer 13. The log retrieving button 73 is used to instruct retrieval of log information. The edit button 74 is used to input or edit relevant information. The search button 75 is used to search information according to a query in the server device 16. A pointer 76 of the mouse is used to input information to any of those buttons or regions.

The washer selection region 72 is for selection of the washers 13 as a source of log information. The washer selection region 72 is designated by the pointer 76 before clicking the mouse, so as to display a list of washers in a pull down form according to registered washers in a washer master file from the server device 16. A desired one of the washers 13 is selected, and indicated specifically in the washer selection region 72.

The log retrieving button 73 is operable to generate a request to the log information retriever 56b for retrieving log information. When the log retrieving button 73 is clicked after designating one of the washers 13, the request for retrieving log information for the designated one of the washers 13 is generated, so the log information retriever 56b performs the task of retrieval. In the present embodiment, one of the washers is designated as source of the log information. However, it is possible to designate two or more of, or all of the washers in connection so as to retrieve log information of such plural washers at one time.

The retrieved washing information is displayed on the log information area 71b. The washing information is indicated in a table form in which one line is assigned to one case. As a default setting, a main key is assigned to the washing serial No. Plural sets of the washing information are indicated in a sequence following an increase in the washing serial No. Unindicated fields of the log information area 71b (data in a data file) can be caused to appear by manual shift of a sliding button 77 to the right or left. It is possible suitably to change a sequence of arranging the fields and the setting of the main key.

The following Table 1 is a log information table as specific example of the log information area 71b in FIG. 6.

TABLE 1

| WASHING SER NO | CATEGORY | DATE | WASHING SEQUENCE (PG_NO) | PATIENT ID | PATIENT'S NAME |
|---|---|---|---|---|---|
| 1 | Wash/disinfect | 8/23 | 1 | A0102 | EMILY YAMADA |
| 2 | Wash/disinfect | 8/24 | 2 | A0312 | THOMAS SUZUKI |
| 3 | Wash/disinfect | 8/25 | 1 | A0045 | HARRY YAMAMOTO |
| 4 | Only disinfect | 8/26 | 4 | A0228 | SOPHIA TANAKA |
| 5 | Wash/disinfect | 8/27 | 1 | | |

| WASHING SER NO | SCOPE ID (SCP_ID) | WASHING OPERATOR | USE OF DISINFECTANT | USE OF FILTER | OPERATION MODE |
|---|---|---|---|---|---|
| 1 | E012 | JOHN FUJI | 1 time | 1 day | Biopsy |
| 2 | E024 | MICHAEL AZABU | 2 times | 2 days | Biopsy |
| 3 | E009 | JOHN FUJI | 3 times | 3 days | Biopsy |
| 4 | E001 | MICHAEL AZABU | 4 times | 4 days | Only observation |
| 5 | | | 1 time | 1 day | |

The washing information with the washing serial No. of 1 to 4 has been read from the server device 16 and is assigned with relevant information such as patient ID and scope ID. Components in the data file are displayed for this washing information. In contrast, the washing information with the washing serial No. of 5 has not yet been assigned with relevant information. Only log information retrieved from the washer 13 is displayed. To input relevant information, the pointer 76 designates washing information as a target, before the edit button 74 is clicked for editing.

Figure 7:
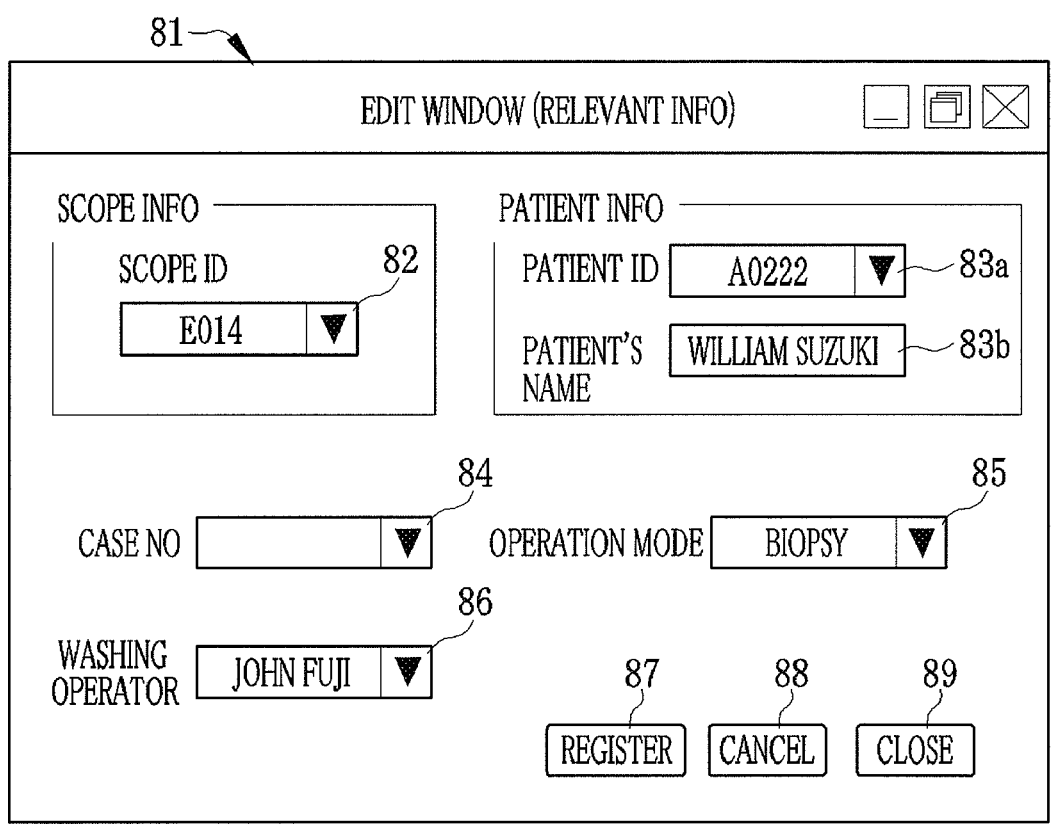
FIG. 7 is a plan illustrating an example of an edit window or relevant information input window.

In FIG. 7, an edit window 81 or relevant information input window is displayed as an editor when the edit button 74 is clicked. In the edit window 81 are arranged a scope ID selection area 82, a patient information areas 83a and 83b, a case number area 84, an operation mode area 85, an operator name area 86, a register button 87, a cancel button 88, and a close button 89. When each of the information areas 82-86 are designated by the pointer 76 and clicked, a master file associated respectively is read from the server device 16, to display a list of previously registered information. Predetermined information is selected in the list, to input various sets of the data, such as the scope ID, patient ID, patient's name, case number of the imaging, operation mode, washing operator's name, and the like.

When the register button 87 is clicked, a command signal for register of input information is generated. The assigning unit 56c assigns the input relevant information to the log information. The washing information after the assignment is stored in the database 26 by recording operation of the server access unit 56d. The cancel button 88 is operable to cancel input information. The close button 89 is operable for closing the edit window 81.

Figure 8:
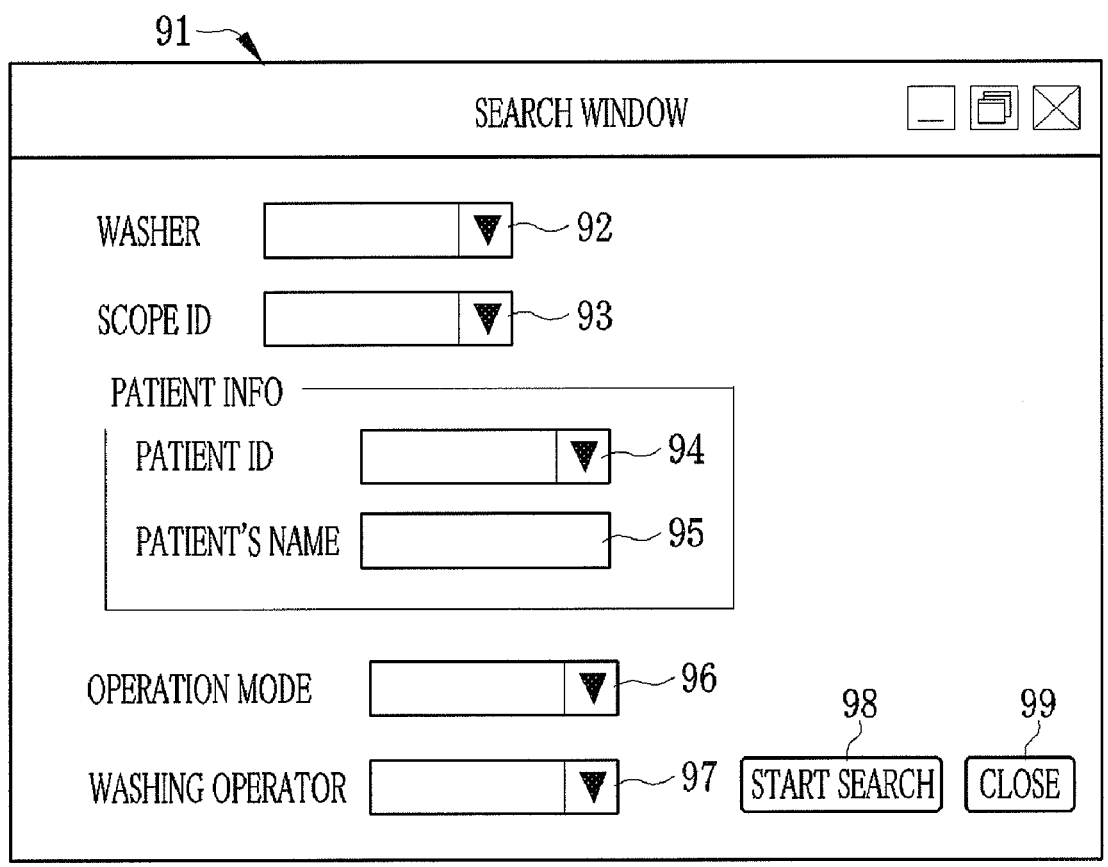
FIG. 8 is a plan illustrating a search window.

In FIG. 8, a search window 91 is for searching washing information from the database 26 of the server device 16 by setting a query, and is displayed when the search button 75 of the washing data managing window 71 is clicked. Input areas 92-97 for inputting information are disposed in the search window 91, the information including a name of the washer, scope ID, patient ID, patient's name, operation mode, washing operator's name and the like. When a search start button 98 is clicked, a request for search is input to the CPU 56. The server access unit 56d sends the request for the search with a query to the server device 16. The server device 16 searches and retrieves washing information according to the query, and sends back a result of the search to the server access unit 56d. The extracted washing information is displayed on the washing data managing window 71. When a close button 99 is clicked, the search window 91 is closed.

Figure 9:
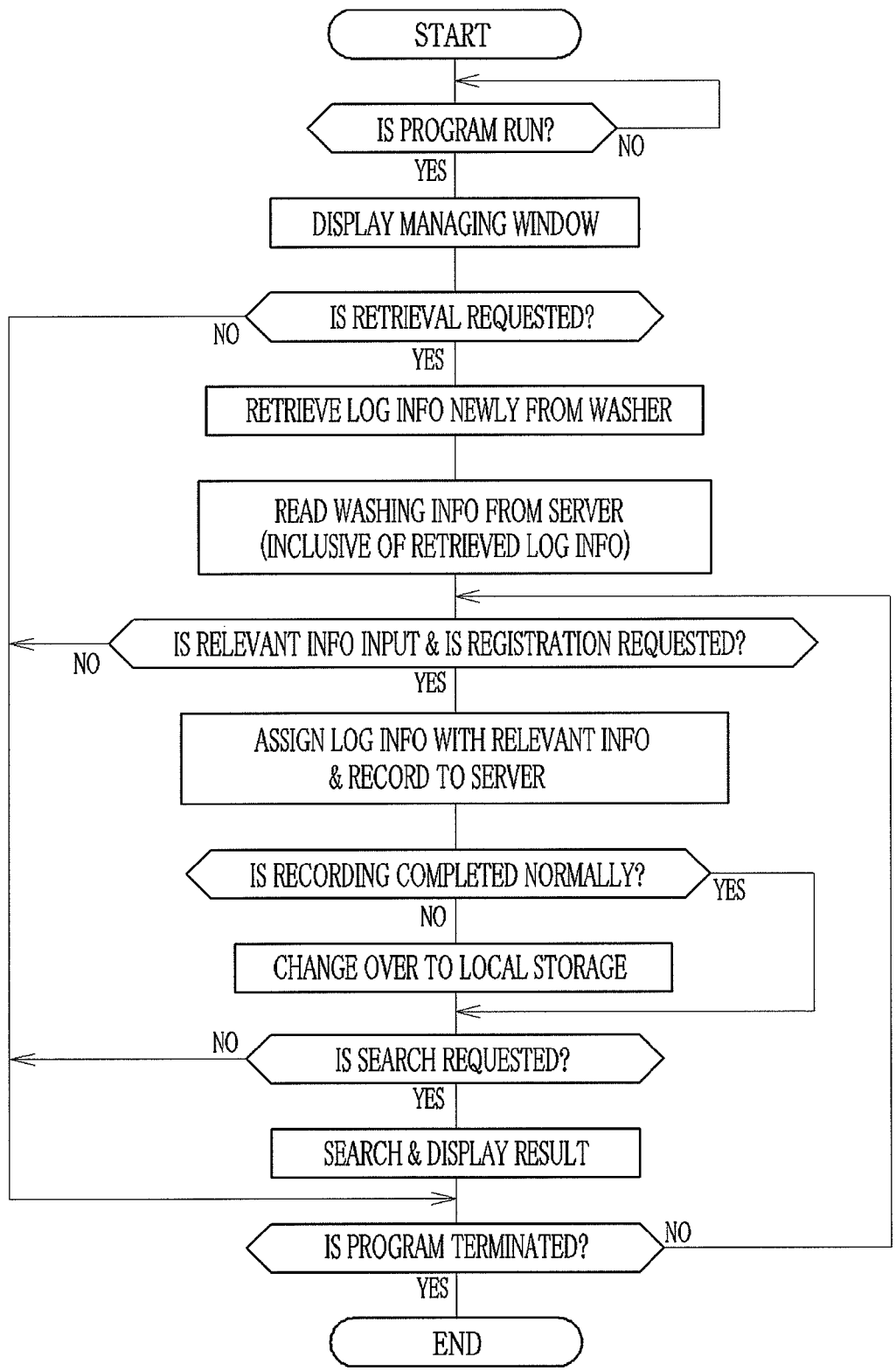
FIG. 9 is a flow chart illustrating steps of the washing data managing.

The operation of the above embodiment is described by referring to FIG. 9. The washing data managing program is run to display the washing data managing window 71 on the console 65. The CPU 56 stands by for inputs. When a request for retrieval is input by use of the log retrieving button 73, the log information retriever 56b retrieves log information from the washer 13 and reads washing information from the server device 16. The log information and washing information are displayed in the log information area 71b. The relevant information is input by use of the edit window 81, to generate a request of registration. Then the assigning unit 56c and the server access unit 56d operate for assignment and recording, so the washing information after the assignment is stored in the database 26.

If there is failure in the normal completion of the recording for storing, then the CPU 56 changes over a target of the storing to the removable auxiliary storage medium 68 as a local media, in which data is stored. When a request for search is input in the search window 91, then the CPU 56 carries out the search, and displays results of the search on the washing data managing window 71.

Thus, the washing information is managed by the data manager 14 according to the invention. Load to the image filing apparatus 12 for this purpose can be reduced in comparison with the known systems. Also, management of the washing information can continue without interrupt even when the image filing apparatus 12 is down, as the image filing apparatus 12 does not perform a task related to managing the washing information. Availability of the system can be maintained. Even when storage of data to the server device 16 is impossible due to failure in the server device 16 or the LAN 24, storage in use can be changed over to enable continuous retrieval of log information from the washer 13. It is possible to prevent overflow of the memory 13c in the washer 13 and to prevent overwriting unretrieved log information.

In the above embodiment, the specification information is common between the washers, the specification information being related to the recording format for recording log information in a washer, and related to communication protocol for a data manager to communicate with a washer for retrieval of log information. However, it is likely that specification information is different between washers, typically in case of a difference between their manufacturers, and a difference in the manufacturing period of those manufactured even by a common manufacturer.

In FIG. 10, an example for solving such problems is illustrated. A washer specification table memory 101 is stored in the hard disk drive 58 or the server device 16 for previously registering specification information of plural washers. At the time of a task of retrieval, the log information retriever 56b accesses the washer specification table memory 101 to carry out the retrieval according to the specifications.

There are washers 102 and 103. In the washer specification table memory 101, a recording format and communication protocol of each of the washers 102 and 103 are written in the washer specification table memory 101 in association with their washer ID. Information of the recording format includes types of components in a data file of the log information recorded by the washers 102 and 103, information of a sequence of the components in the data file, partition information of the components in the data file, the total number of bytes of the log information, byte numbers assigned to respectively the components in the data file, and the like. The log information retriever 56b extracts components in the data file by analyzing the retrieved log information according to the recording format of the selected washer, and carries out conversion of the components in the data file into a common format.

The protocol of communication is constituted by plural layers according to the OSI (Open Systems Interconnection) reference model determined by the ISO, the layers including a physical layer where the physical interface is determined for the shape of a connector, the number of signal lines and the like, and an upper layer for determining the protocol of the communication application operating on the OS (Operating System). The protocol of the upper layer may differ even when the physical layer is common. The washer specification table memory 101 stores protocol information of a layer required for retrieving the log information. The log information retriever 56b accesses the washer specification table memory 101, and retrieves information by control of communication according to the communication protocol corresponding to a designated one of the washers.

In FIG. 11, an embodiment in which different physical interfaces are used is illustrated. An interface converter 104 is provided, and has plural interface ports 104a and 104b of communication interfaces associated with particular physical interfaces different from one another. A protocol for the interface converter 104 is used between the interface ports 104 a and 104b and washers 106 and 107 connected thereto. The interface converter 104 carries out conversion to the protocol with which the data manager 14 is compatible. Thus, any of the washers 106 and 107 can be connected with the data manager 14 in spite of the difference between the physical interfaces. A protocol of a layer which is not supported by the interface converter 104 is previously stored in the washer specification table memory 101 even when the interface converter 104 is used.

In the present system for endoscope data management, log information of all of the plural washers can be managed as entirety, because the system for endoscope data management is on line with the washers which have specifications different from one another. Also, only either one of the recording format and communication protocol may be stored in the washer specification table memory 101 instead of storing both of those according to the embodiment.

In the above embodiment, a bar code reader reads and retrieves the scope ID. Also, it is possible in a preferred embodiment to read a scope ID by use of the system of the RFID or radio frequency identification. An RFID tag 108 is associated with the endoscope 17 and stores the scope ID. An RFID reader 109 is incorporated in each of the washers 106 and 107, and reads and retrieves the scope ID from the RFID tag 108. A memory 110 is associated with each of the washers 106 and 107, and stores the scope ID as log information. The scope ID is retrieved by the log information retriever 56b of the data manager 14. Note that an RFID reader may be incorporated in the data manager 14 instead of the washer.

Note that a large-capacity storage device of any type may be used on line through the network in place of the server device 16 of the above embodiment, and may be a slave unit, storage or device used according to the well-known technique of managing databases.

In the embodiments, the relevant information is input by use of the edit window 81 to edit the log information by adding components of relevant information. Furthermore, editing of the log information as a term used in the present invention can be alteration or deletion of components of relevant information, and also can be duplication of log information to be stored, changes in location of its storage, changes in the file name or sequence of components, and other changes in the property of a data file of the log information as well-known editing operation in techniques of the network.

In the above embodiments, the system for endoscope data management is established in one hospital. Furthermore, the hospital may be constituted by a plurality of sites geographically separate from one another. For such sites, the data manager, the image filing apparatus, the server and the like of the above-described system for endoscope data management may be disposed in the sites discretely from one another. Also, a plurality of hospitals may be linked. For such hospitals, the data manager, the image filing apparatus, the server and the like of the above-described system for endoscope data management may be disposed in the hospitals discretely from one another. To this end, a communication network may be a wide area network in place of the LAN or a closed network. In combination with the wide area network, the VPN (Virtual Private Network) can be established for the purpose of ensuring security. In conclusion, a system for endoscope data management can be flexibly established in the invention in comparison with known data managing systems, because the data manager is individual from the washer and the image filing apparatus. Communication between the apparatuses may be wireless. The communication network may be a wireless network.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A data manager for washing data management of washing of an endoscope, comprising:
    a data retriever for retrieving log information of said washing by communication with washers for washing respectively said endoscope;
    an assigning unit for recording endoscope identification information assigned to said endoscope and said log information in association with one another;
    a designator for designating one of said washers associated with said log information being retrieved; and
    further comprising an access unit for accessing a washer specification table memory to read specification information being related to at least one of a recording format of recording said log information in said washers and information of a communication method of said washers;
    wherein said data retriever refers to said specification information in said washer specification table memory, to retrieve said log information from said washer designated by said designator.

2. A data manager as defined in claim 1, further comprising an editor for editing said log information of said designated washer.

3. A data manager as defined in claim 1, further comprising a storage changer for operating upon occurrence of failure in writing of said log information, and for changeover to an auxiliary storage medium to write said log information thereto.

4. A data manager as defined in claim 3, wherein said auxiliary storage medium is locally connected, and in case of failure in normal completion of writing to a storage medium on line through a network, said storage changer changes over to said auxiliary storage medium.

5. A data manager as defined in claim 1, further comprising a reader for reading said endoscope identification information from said endoscope.

* * * * *